United States Patent
Cuthbertson

(10) Patent No.: US 6,906,171 B2
(45) Date of Patent: Jun. 14, 2005

(54) PROCESS FOR THE DEPROTECTION OF PROTECTED THIOLS

(75) Inventor: Alan Cuthbertson, Oslo (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 10/052,300

(22) Filed: Jan. 18, 2002

(65) Prior Publication Data

US 2002/0143207 A1 Oct. 3, 2002

Related U.S. Application Data

(63) Continuation of application No. PCT/GB00/02796, filed on Jul. 19, 2000.
(60) Provisional application No. 60/146,866, filed on Aug. 3, 1999.

(30) Foreign Application Priority Data

| Jul. 19, 1999 | (GB) | 9916919 |
| Feb. 18, 2000 | (GB) | 0003926 |
| Mar. 31, 2000 | (GB) | 0007865 |

(51) Int. Cl.$^7$ .......................... A61K 38/00; C07S 5/00; C07C 319/24
(52) U.S. Cl. .................. 530/336; 530/336; 530/332; 562/426; 562/556; 568/21
(58) Field of Search ................... 530/336, 332, 530/335, 333, 337, 930; 562/426, 556; 568/21

(56) References Cited

PUBLICATIONS

Koide et al. 1993. Chem. Pharm. Bull. vol. 41, No. 6, pp. 1030–1034.*
Musiol et al. 1994. Biopolymers, Vo. 34, pp. 1553–1562.*
Barany and Merrifield "The Peptides" vol. 2, Ed. Gross and Minehoffer, Academic Press, pp. 233–240 (1980).
Veber, et.al. in J. Am. Chem. Soc. 94, pp. 5456–5461 (1972).
Van Rietschoten, et.al. "Cysteine Protection in Solid Phase Synthesis of Apamin" pp. 522–524 (1977).
Singh, et.al. Tetrahedron Letters. vol. 37, No. 24, pp. 4117–4120 (1996).
Otaka, et.al. Tetrahedron Letters, vol. 32, No. 9 pp. 1223–1226 (1991).
Akaji, et.al. J. Am. Chem. Soc., vol. 114, No. 11, pp. 4137–4143 (1992).
Sieber, et.al. Helv. Chim Cata. 57 pp. 2617–2621 (1974).
Atherton, et.al. J. Chem. Soc. Perkin Trans. 1, p. 2065 (1985).
Akaji, et.al. J. Am. Chem. Soc. 115, p. 11384 (1993).
Hargittai, et.al., J. Peptide Res. 54, pp. 468–479 (1999).
Tam, et.al. J. Am. Chem Soc. 113, p. 6657–6662 (1991).
Cuthbertson, et.al. Tetrahedron Letters, 41 pp. 3661–3663 (2000).
Tamamura, et.al., Intl Journal of Peptide & Protein Research, 45, No. 4, pp. 312–319 (1995).

* cited by examiner

*Primary Examiner*—Christopher R. Tate
*Assistant Examiner*—B. Dell Chism
(74) *Attorney, Agent, or Firm*—Li Cai

(57) ABSTRACT

The synthesis of peptides comprising disulphide bridges is challenging since it is difficult to ensure that the correct cysteine residues combine to form the desired disulphide bridges. The present invention describes novel protection techniques useful in the preparation of peptides. Described is a process for the deprotection of an Acm-, MBzl- and/or tBu-protected thiol which comprises reacting said protected thiol with an acid in the presence of an oxidising agent at a temperature sufficient to effect deprotection and generation of disulphide bonds.

9 Claims, No Drawings

PROCESS FOR THE DEPROTECTION OF PROTECTED THIOLS

This application is a continuation application of international application number PCT/GB00/02796 filed Jul. 19, 2000, the entire disclosure of which is hereby incorporated by reference. This Application also claims the benefit of Provisional Application No. 60/146,866, filed Aug. 3, 1999.

This invention relates to a new process for the deprotection of protected thiol compounds, more particularly thiols protected by acetamidomethyl, 4-methylbenzyl and t-butyl groups (hereinafter referred to as Acm, MBzl and tBu respectively), with concomitant oxidation of the deprotected thiols to form disulphides. Such processes are particularly useful in peptide synthesis.

During organic syntheses it is quite routine for certain reactive functionalities to be protected to prevent their participation in unwanted side reactions. For example, reactive carbonyl functionalities are often protected as ketals, and reactive hydroxyl and carboxyl groups are often protected as esters.

The neutral but strongly nucleophilic thiol group present in cysteine generally requires protection during peptide syntheses. A wide variety of thiol protecting groups are known, including benzyl, MBzl, 4-methoxybenzyl, trityl, methoxytrityl, tBu, t-butylthiol, acetyl, 3-nitro-2-pyridinesulphenyl and Acm. All these groups have been successfully used in peptide synthesis and are reviewed by Barany and Merrifield in "The Peptides" Vol. 2, Ed. Gross and Minehoffer, Academic Press, pp. 233–240 (1980).

Acm is a thiol protecting group which is normally removed by oxidative cleavage, for example by treatment with mercury (II), iodine, silver (I) or thallium (III). It is generally regarded as acid stable since, although acidolytic cleavage of Acm is theoretically possible in anhydrous or aqueous acids, such reactions are inconveniently slow in practice because of difficulties in protonating the sulphur atom.

In this context Fujii et al. in Chem. Pharm. Bull. 41(6), pp. 1030–1034 (1993) describe the synthesis and oxidation of oxytocin using Cys(Acm) and trifluoroacetic acid (TFA)/10% dimethyl sulphoxide (DMSO). The authors state that Cys(Acm)-oxytocin survived nearly intact after a 12 hour treatment in the above TFA/DMSO mixture, showing that Acm protection is stable under such acid conditions. The S-Acm group was also reported by Veber et al. in J. Am. Chem. Soc. 94, pp. 5456–5461 (1972) as being stable to hydrofluoric acid (HF) and strong nucleophiles such as hydrazine.

Van Rietschoten et al. reported in Peptides (1977), pp. 522–524 that treatment of a peptide containing four Acm groups with HF-anisole resulted in 20% of the Acm groups being removed. More recently, Fisher et al. in J. Pep. Res. 49(4), pp. 341–346 (1997) have described a modification to a tyrosine residue due to acidolytic cleavage of Acm, and Singh et al. in Tetrahedron Letters Vol. 37, No. 24, pp. 4117–4120 (1996) report on the partial acidolytic cleavage of Acm from C-terminal Cys(Acm) peptides. These acid-induced deprotection reactions are regarded as unwanted side reactions during peptide cleavage.

The MBzl thiol protecting group is traditionally cleaved using strong acids such as HF at a temperature of −5° C. to 0° C. Otaka et al. in Tetrahedron Letters Vol. 32, No. 9, pp. 1223–1226 (1991) report that the MBzl group is stable to TFA and that MBzl-protected cysteine is not converted to cystine upon treatment with TFA/10% DMSO at room temperature.

The tBu thiol protecting group is typically removed by oxidative cleavage, e.g. by treatment with mercury (II), or by acidolysis with trifluoromethane sulphonic acid. The group is considered to be stable to TFA and to iodine oxidation.

Although Akaji et al. in J. Am. Chem. Soc., Vol. 114, No. 11, pp. 4137–4143 (1992) report the acidolytic removal of a variety of cysteine protecting groups including MBzl, tBu and Acm, the reaction is dependent on the presence of a suitable silyl chloride.

SUMMARY OF INVENTION

The present invention is based on the unexpected finding that Acm, MBzl and tBu thiol protecting groups are labile to acids under oxidising conditions, particularly as the reaction temperature is increased. Thus tBu thiol protecting groups may be rapidly cleaved in this way at room temperature and even more rapidly at elevated temperatures. Acm and MBzl thiol protecting groups become increasingly labile under such conditions at temperatures in excess of 30° C., particularly at temperatures of 50° C. and above, such that it is possible to achieve substantially quantitative deprotection with reaction times of a few hours or less. Such acid-induced deprotection is particularly advantageous in that it avoids the need for use of the more toxic reagents currently employed to remove Acm, MBzl and tBu groups. By conducting the deprotection in the presence of an oxidising agent the liberated thiol groups are converted directly to intermolecular or intramolecular disulphide groups; as discussed hereinafter this has particularly valuable applications in the synthesis of cyclic peptides containing disulphide linkages.

DETAILED DESCRIPTION OF THE INVENTION

Thus, according to one aspect, the invention provides a process for the deprotection of an Acm-, MBzl- and/or tBu-protected thiol which comprises reacting said protected thiol with an acid in the presence of an oxidising agent at a temperature sufficient to effect deprotection and generation of disulphide bonds.

Both aqueous and anhydrous acids may be used in the process. Thus, for example, aqueous inorganic acids, e.g. mineral acids such as hydrochloric acid, and aqueous or anhydrous organic acids, e.g. carboxylic acids such as acetic acid or, more preferably, strong carboxylic acids such as TFA, and sulphonic acids such as methanesulphonic acid may be useful.

DMSO is a preferred example of an oxidising agent useful in the process. Other sulphoxides such as tetramethylenesulphoxide may also be useful, as may metal superoxides and peroxides such as potassium superoxide or nickel peroxide, thiocarbonates such as sodium trithiocarbonate and organometallic carbonates such as triphenylbismuth carbonate.

In a preferred embodiment the thiol to be deprotected is a peptide containing one or more Acm-, MBzl- and/or tBu-protected cysteine residues.

Peptides represent a class of molecules which are extremely well suited for the targeting of disease specific markers in vivo, and considerable attention is being given to the preparation of synthetic peptides as potential components of targeted imaging agents.

The synthesis of cysteine-containing peptides presents special challenges to a peptide chemist as the peptide can exist in either a reduced or an oxidised state. Oxidised peptides containing more than one cysteine residue may form intramolecular disulphides or intermolecular disulphides such as dimers, trimers or multimers. Thus, for example, a peptide containing six cysteine residues is potentially capable of forming 15 disulphide isomers, and careful planning and selection of suitable protection strategy is therefore required if correct disulphide pairings are to be achieved in such peptides. It will be appreciated that correct pairing is frequently critical to correct folding of the peptide backbone and concomitant orientation of side chain functionalities in order to give a biologically active conformation capable of high affinity receptor binding.

Typical existing strategies for the selective formation of two or more disulphide bonds use combinations of protecting groups such as trityl and Acm or t-butylthio and Acm, the first disulphide bond being formed after removal of the trityl or t-butylthio groups and the second being formed by oxidative cleavage of the Acm groups using, for example, iodine or thallium trifluoroacetate. Other examples of the synthesis of multibridged peptides include the solution synthesis of insulin by Sieber et al. described in Helv. Chim. Acta. 57, pp. 2617–2621 (1974) and the procedures of Atherton et al., J. Chem. Soc. Perkin Trans. 1, p. 2065 (1985) and Akaji et al., J. Am. Chem. Soc. 115, p. 11384 (1993).

Deprotection in accordance with the present invention permits considerable simplification of such strategies, such that two or more disulphide bonds may be generated in a "one pot" reaction, thereby avoiding the need for intermediate purification of partially oxidised or partially protected peptides and so achieving savings in solvent use and time and improvements in product yield. Thus, by preparing a peptide containing two acid-labile thiol protecting groups (e.g. trityl groups) as well as two or more Acm and/or MBzl groups, a first disulphide bond may be formed by acid treatment of the peptide at a relatively low (e.g. ambient) temperature and one or more further disulphide bonds may be formed simply by increasing the temperature of the reaction mixture to a temperature in excess of 30° C. such that the Acm and/or MBzl groups are cleaved. The required oxidising agent may be added before or after the low temperature treatment, as desired.

The positions of the acid-labile protecting groups are advantageously such that the first-formed disulphide bond brings the molecule into a folded conformation such that the remaining Acm-protected and/or MBzl-protected thiol groups are juxtaposed in a manner which facilitates correct formation of the remaining disulphide bond or bonds.

Since, as noted above, tBu thiol protecting groups are readily cleaved at room temperature by acidic and oxidative treatment, a combination of tBu with Acm and/or MBzl protection may be used, with the tBu groups being cleaved at room temperature and the Acm and/or MBzl groups subsequently being removed upon heating to a temperature above 30° C. The specific formation of multiple disulphides may therefore be effected in high yield using a "one pot" strategy without the need for isolating intermediates by chromatography.

The use of TFA/DMSO mixtures, e.g. with a DMSO content of 1 to 20%, e.g. 2–10%, to promote deprotection and disulphide bond formation is particularly preferred in such embodiments of the invention, since both the S-protected starting materials and the disulphide linked intermediates and end products will typically be soluble in such mixtures. Both TFA and DMSO may readily be recycled for further use.

The fact that thiol protecting groups such as trityl and methoxytrityl are generally acid labile, whilst tBu thiol protecting groups are only acid labile under oxidising conditions may be exploited in the synthesis of peptides containing three disulphide bonds by a regioselective "one pot" oxidation process. Thus a resin-supported synthetic peptide containing appropriately positioned pairs of cysteine residues protected with trityl, methoxytrityl or other acid labile groups, with tBu groups and with Acm and/or MBzl groups repectively may initially be treated with acid to effect cleavage from the resin and cleavage of the trityl, methoxytrityl or other acid labile protecting groups. The thus-generated pair of thiol groups may be oxidised in aqueous solution at basic pH or in aqueous DMSO to form the first desired disulphide bond, whereafter the solvent may be evaporated in vacuo or by freeze drying. Successive low (e.g. room) temperature and high (i.e. _30° C.) temperature acidic and oxidative treatment of the product as described above then leads to formation of the desired second and third disulphide bonds by successive reaction of the tBu-protected and Acm-and/or MBzl-protected pairs of thiol groups.

The present procedure allows cysteine-containing peptides to be oxidised at concentrations in excess of 1 mg/ml, thereby substantially reducing solvent volume requirements compared to existing protocols such as iodine cleavage of Acm and air oxidation, which typically employ peptide concentrations of the order of 0.1 mg/ml and so require the product to be concentrated, e.g. by ion exchange chromatography, prior to final purification. In accordance with the present procedure, on the other hand, product concentration may be effected simply by solvent evaporation in vacuo.

EXAMPLES

The following non-limitative Examples serve to illustrate the invention, but are not intended to be illustrative of all embodiments.

EXAMPLE 1

"One Pot" Synthesis of α-conotoxin SI [Ile-Cys-Cys-Asn-Pro-Ala-Cys-Gly-Pro-Lys-Tyr-Ser-Cys-$NH_2$, with disulphide bonds connecting Cys 2 with Cys 7 and Cys 3 with Cys 13]

Purification on a Vydac 218TP152010 semi-preparative column using a gradient of 0 to 30% B over 30 minutes (A=0.1% TFA/water and B=0.1% TFA/acetonitrile) at a flow rate of 5 ml/minute, followed by freeze-drying, afforded conotoxin (0.7 mg, 35% yield) which was found to be >90% pure. Further characterisation was carried out using MALDI 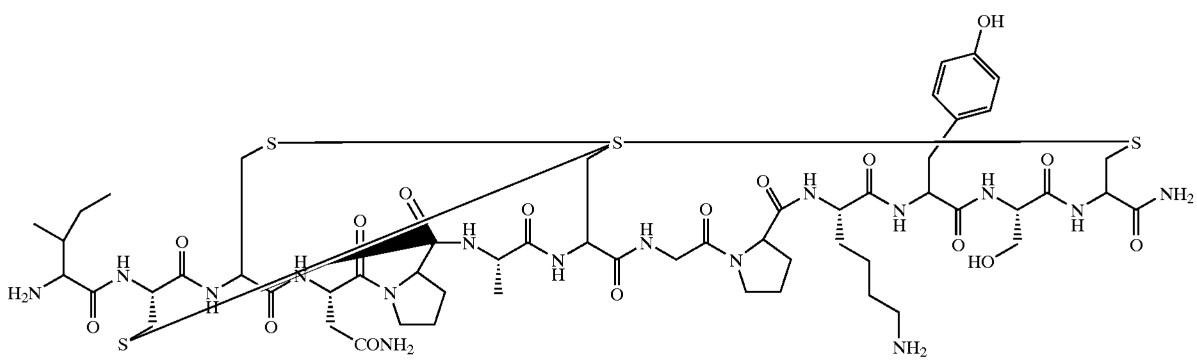 The peptide sequence was assembled on an ABI 433A automatic peptide synthesiser starting with Rink amide resin (Novabiochem) on a 0.12 mmol scale using 1 mmol amino acid cartridges. Cysteine residues 2 and 7 were protected with trityl groups, while residues 3 and 13 were protected with acetamidomethyl groups. All amino acids were pre-activated using O-Benzotriazol-1-yl-N,N,N',N'-tetramethyluronium hexafluorophosphate (HBTU).

Simultaneous removal of the peptide from the resin and the side-chain protecting groups (except Acm) from the peptide was effected by treatment with trifluoroacetic acid (TFA) containing 5% triisopropylsilane and 5% water for 2 hours, giving a crude product yield of 130 mg. HPLC analysis of the crude product (Vydac 218TP54 column) was carried out using a gradient of 5 to 30% B over 20 minutes (A=0.1% TFA/water and B=0.1% TFA/acetonitrile) at a flow rate of 1 ml/minute; the product was found to be >90% pure. Further product characterisation was carried out using MALDI mass spectrometry: M+H for Acm protected product expected at 1496, found at 1502.

To 2 mg of the crude product were added TFA (10 ml) and dimethyl sulphoxide (DMSO) (0.1 ml). The mixture was stirred on ice and the course of oxidation was followed by HPLC. The starting product, retention time 16.2 minutes (0 to 30% B over 20 minutes where A=0.1% TFA/water and B=0.1% TFA/acetonitrile), was slowly replaced by a new product with a retention time of 16.4 minutes, and after 2 hours the starting product had completely disappeared. 0.05 ml of anisole was then added to the peptide solution, and the mixture was warmed to 60° C. for a further 2 hours, whereafter the TFA was removed in vacuo and the peptide was precipitated by the addition of diethyl ether. The crude fully oxidised material (1.4 mg) comprised 2 main products, ratio 1:5, with HPLC retention times of 16.9 and 17.8 minutes respectively. The 17.8 minute product, comprising ca. 80% of the material, was found to co-elute with an authentic sample of α-conotoxin (Bachem, H-1112).mass spectrometry: M+H for product expected at 1354, found at 1356.

EXAMPLE 2

"One Pot" Synthesis of α-conotoxin SI

The peptide sequence was assembled as described in Example 1 except that cysteine residues 2 and 7 were protected with t-butyl groups, while residues 3 and 13 were protected with 4-methylbenzyl groups. All amino acids were pre-activated using HBTU.

Simultaneous removal of the peptide from the resin and the side-chain protecting groups (except t-butyl and 4-methylbenzul) from the peptide was effected by treatment with TFA containing 5% triisopropylsilane and 5% water for 2 hours, giving a crude product yield of 125 mg. HPLC analysis of the crude product (Vydac 218TP54 column) was carried out using a gradient of 20 to 60% B over 20 minutes (A=0.1% TFA/water and B=0.1% TFA/acetonitrile) at a flow rate of 1 ml/minute; the product was found to have a retention time of 15.7 minutes and purity >90%. Further product characterisation was carried out using MALDI mass spectrometry: M+H for partially protected product expected at 1680, found at 1685.

To 50 mg of the crude partially protected product in a clean flask were added TFA (98 ml), DMSO (2.0 ml) and anisole (0.1 mL). The mixture was stirred at room temperature for 40 minutes and a sample of the reaction mixture was run on a MALDI mass spectrometer. A new product appeared which was confirmed to be the single disulphide with the 4-methylbenzyl protecting groups remaining: M+H for partially protected product expected at 1565, found at 1568.

The flask was then placed in an oil bath and heated to 70° C. for 3 hours, following which the TFA was removed in vacuo and the peptide was precipitated by the addition of diethyl ether. The precipitate was trituratyed with ether and air-dried to give crude fully oxidised product (45 mg) in almost quantitative yield and with an HPLC purity of >90%.

An aliquot of 20 mg of the crude fully oxidised product was purified by preparative HPLC on a Vydac 218TP1022 C18 preparative column using a gradient of 0 to 30% B over 40 minutes (A=0.1% TFA/water and B=0.1% TFA/acetonitrile) at a flow rate of 9 ml/minute. The fractions containing pure product were collected and freeze-dried (10 mg, 50% yield). The product was found to be >99% pure by analytical HPLC. Further characterisation was carried out using MALDI mass spectrometry: M+H for product expected at 1354, found at 1356.

The material was shown to co-elute with an authentic sample of α-conotoxin (Bachem, H-1112).

EXAMPLE 3

Synthesis of Oxytocin a) Synthesis of Cys(Acm)-protected Oxytocin: $NH_2$-Cys(Acm)-Tyr-Ile-Gln-Asn-Cys(Acm)-Pro-Leu-Gly-$NH_2$

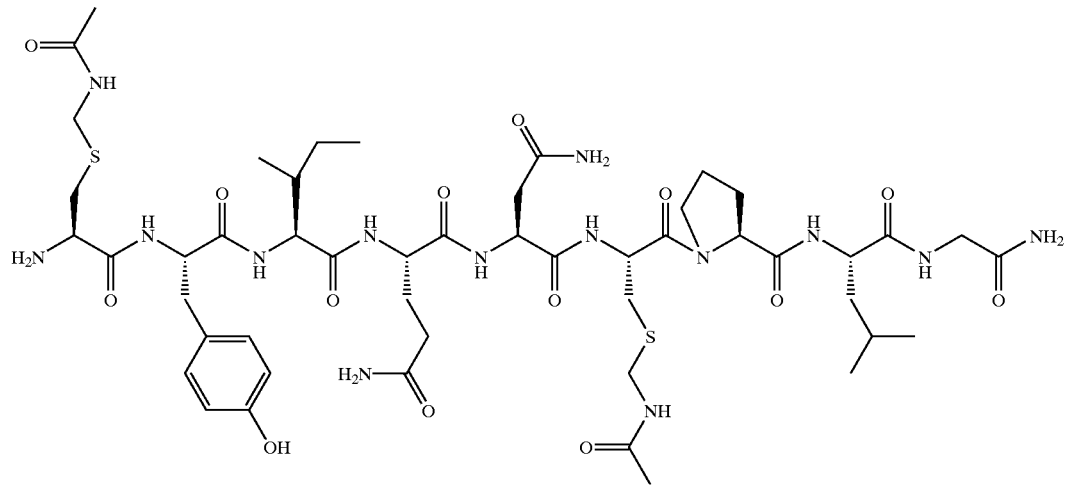

The peptide was synthesised on a ABI 433A automatic peptide synthesiser starting with Rink amide AM resin on a 0.25 mmol scale using 1 mmol amino acid cartridges. The amino acids were pre-activated using HBTU before coupling. Simultaneous removal of the peptide from the resin and the side-chain protecting groups (except Acm) from the peptide was effected by treatment with TFA containing 5% triisopropylsilane and 5% water for one hour.

The resulting crude naterial (300 mg) was purified by preparative HPLC (Vydac C18 218TP1022 column) using a gradient of 5 to 30% B over 40 minutes (A=0.1% TFA/water and B=0.1% TFA/acetonitrile) at a flow rate of 9 ml/minute. After lyophilization 166 mg of pure material was obtained. HPLC analysis of this purified product (Vydac C18 218TP54 column) was carried out using a gradient of 5 to 50% B (A=0.1% TFA/water and B=0.1% TFA/acetonitrile) with product detection by UV at 214 nm; the product retention time was 14.30 minutes. Further product characterisation was carried out using MALDI mass spectrometry: M+H for product expected at 1151.0, found at 1551.5.

b) Deprotection and oxidation to form oxytocin [$NH_2$-Cys-Tyr-Ile-Gln-Asn-Cys-Pro-Leu-Gly-$NH_2$, with disulphide bond connecting Cys 1 with Cys 6]

5 mg of Cys(Acm)-protected oxytocin was dissolved in TFA (2 ml) then added to a mixture of anisole (40 μl), DMSO (1 ml) and TFA (18 ml) preheated to 60° C. After 5 hours at this temperature the occurence of quantitative conversion to oxytocin was confirmed by analytical HPLC (Vydac C18 218TP54 column) using a gradient of 5 to 50% B (A=0.1% TFA/water and B=0.1% TFA/acetonitrile) with product detection by UV at 214 nm; the product retention time was 12.98 minutes. Further product characterisation was carried out using MALDI mass spectrometry: M+H for product expected at 1007, found at 1011. The product was found to co-elute with an authentic sample of oxytocin purchased form Novabiochem.

EXAMPLE 4

Comparative Study of Deprotection and Oxidation Rates of Cysteine-protected Oxytocin Analogues at Room Temperature and 60° C.

The procedure of Example 3(a) was repeated to prepare Cys(tBu)-protected and Cys(MBzl)-protected analogues of oxytocin. Deprotection and oxidation of these analogues and Cys(Acm)-protected oxytocin were carried out as described in Example 3(b) at room temperature and at 60° C. The following table summarises the extent of conversion to oxytocin as determined by analytical HPLC; the occurence of quantitative conversion at 60° C. was confirmed by MALDI mass spectrometry.

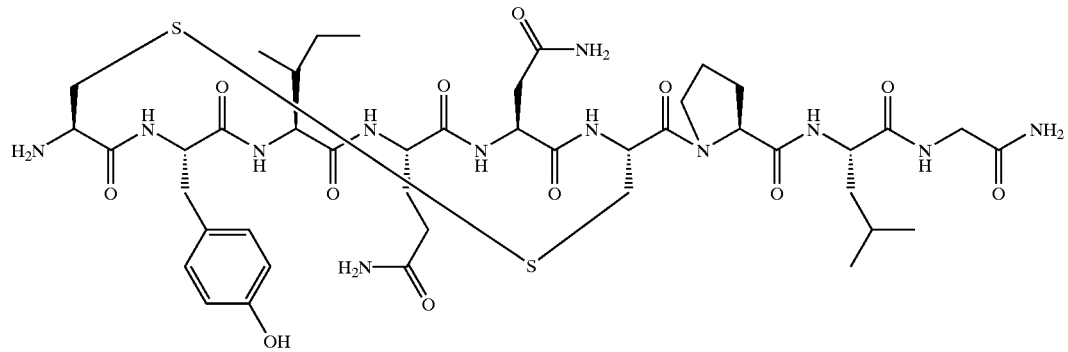

| Protecting group | % oxytocin formed at room temperature | % oxytocin formed at 60° C. |
| --- | --- | --- |
| tBu | 100% after 40 min. | 100% after 10 min. |
| Acm | 45% after 72 hours | 100% after 5 hours |
| MBzl | 30% after 72 hours | 100% after 6 hours |

EXAMPLE 5

"One pot" synthesis of heat stable enterotoxin ST peptide [NH$_2$-Cys-Cys-Glu-Leu-Cys-Cys-Asn-Pro-Ala-Cys-Ala-Gly-Cys-Tyr-OH with disulphide bonds connecting Cys 1 with Cys 6, Cys 2 with Cys 10 and Cys 5 with Cys 13]

The peptide sequence was assembled in similar manner to that described in Example 1; cysteine residues 1 and 6 were protected with trityl groups, residues 2 and 10 with t butyl groups and residues 5 and 13 with 4-methylbenzyl groups. The peptide was cleaved from the solid support as described in Example 1, with a crude yield of 190 mg (cysteine residues 1 and 6 in the thiol form, the remaining cysteines still protected). 50 mg of the crude partially protected peptide were dissolved in 400 ml of water/acetonitrile (60:40) and the pH was adjusted to 8 by addition of dilute ammonium hydroxide. DMSO (10 ml) was added and the course of the ensuing oxidation was followed by analytical HPLC and MALDI-TOF. A new product with a disulphide bond connecting Cys 1 with Cys 6 was found to form within 1 hour, whereafter the solvent was removed in vacuo.

To the resulting DMSO-containing residue in the same flask were added TFA (75 ml) and anisole (0.1 ml), and the mixture was stirred for 1 hour. MALDI-TOF analysis showed that the t-butyl groups had been removed and that a second disulphide bond had formed connecting Cys 2 with Cys 10. The flask was then fitted with a condenser and the temperature was raised to 70° C. for 1 hour. MALDI-TOF analysis revealed that complete cleavage of the 4-methylbenzyl groups had taken place. The TFA was removed and the product was precipitated by addition of diethyl ether. Crude product was recovered following trituration with diethyl ether and air drying. Purification by HPLC yielded pure product in 30% yield.

The product was shown to co-elute with an authentic sample of ST peptide and was confirmed to be active (Ki=3 nM) in an in vitro screening assay.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A process the for the preparation of a compound comprising at least two disulphide bonds from a precursor having at least two pairs of thiol groups, each pair of thiol groups being protected with different thiol-protecting groups selected from acetamidomethyl (Acm), 4-methylbenzyl (MBzl) and t-butyl (tBu), said process comprising:

(i) reaction of the precursor with an acid in the presence of an oxidising agent at a first temperature sufficient to effect deprotection of tBu protected thiols and disulphide bond formation for a first pair of protected thiol groups;

(ii) raising the temperature of the reaction mixture from step (i) to a second temperature sufficient to effect deprotection of Acm and/or MBzl protected thiols and disulphide bond formation for a second pair of protected thiol groups.

2. A process as claimed in claim 1 wherein said acid is trifluoroacetic acid (TFA).

3. A process as claimed in either one of claim 1 wherein said oxidising agent is dimethyl sulphoxide (DMSO).

4. A process as claimed in any one of claim 1 wherein deprotection is effected using a TFA/DMSO mixture comprising 1 to 20% DMSO.

5. A process as claimed in any one of claim 1 wherein said protected thiol is present in a peptide.

6. A process as claimed in claim 5 wherein said peptide comprises at least two tBu protected thiols and/or at least two Acm or MBzl protected thiols.

7. A process as claimed in any of claim 1 wherein tBu protected thiols are deprotected at room temperature in step (i).

8. A process as claimed in any one of claim 1 wherein Acm or MBzl protected thiols are deprotected at temperatures of 30–50° C., in step (ii).

9. A process as claimed in claim 8 wherein Acm or MBzl protected thiols are deprotected at temperatures of 50–70° C., in step (ii).

* * * * *